United States Patent
Coleman et al.

(10) Patent No.: US 10,182,965 B2
(45) Date of Patent: *Jan. 22, 2019

(54) PROGRAMMABLE CARDIOPULMONARY RESUSCITATION (CPR) DETECTION DEVICE

(71) Applicant: Physio-Control, Inc., Redmond, WA (US)

(72) Inventors: Micha Coleman, Woodinville, WA (US); Richard C. Nova, Kirkland, WA (US); Maegan P. Wilkinson, Seattle, WA (US); John C. Daynes, Redmond, WA (US); Ryan W. Apperson, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 652 days.

This patent is subject to a terminal disclaimer.

(21) Appl. No.: 14/837,773

(22) Filed: Aug. 27, 2015

(65) Prior Publication Data

US 2015/0366750 A1     Dec. 24, 2015

Related U.S. Application Data

(63) Continuation of application No. 13/306,933, filed on Nov. 29, 2011, now Pat. No. 9,149,411.

(Continued)

(51) Int. Cl.
  *A61H 31/00* (2006.01)
  *A61N 1/39* (2006.01)
(Continued)

(52) U.S. Cl.
  CPC ........... *A61H 31/005* (2013.01); *A61B 5/11* (2013.01); *A61B 5/6843* (2013.01); *A61B 5/742* (2013.01);
(Continued)

(58) Field of Classification Search
  CPC ............ A61H 31/005; A61H 31/007; A61H 2201/5079; A61H 2201/5076;
(Continued)

(56) References Cited

U.S. PATENT DOCUMENTS 9,149,411 B2 * 10/2015 Coleman ............. A61N 1/3993
2006/0270952 A1   11/2006 Freeman et al.
(Continued)

*Primary Examiner* — Quang D Thanh
(74) *Attorney, Agent, or Firm* — Lane Powell PC

(57) ABSTRACT

Time after time studies find that often, even when administered by trained professionals, cardiopulmonary resuscitation (CPR) compression rates and depth are inadequate. Too week, shallow or too forceful compressions may contribute to suboptimal patient outcome. Several parameters are crucial for optimal and properly-administered CPR. Crucial parameters include proper hand positioning on the patient's chest, depth of compression of 4-5 cm, and compression rate of 100 compressions per minute. The crucial parameters are often affected by patient parameters, and relative to the patient, rescuer parameters, such as patient thoracic volume; weight; age; gender; and rescuer's, relative to the patient's, parameters, such as weight, height; physical form, etc. Proposed is an automated CPR feedback device with user programmable settings for assisting with real-time feedback and subsequently correcting rescuers patient customized CPR technique.

7 Claims, 5 Drawing Sheets

Related U.S. Application Data

(60) Provisional application No. 61/417,801, filed on Nov. 29, 2010.

(51) Int. Cl.
    *A61N 1/372*     (2006.01)
    *A61B 5/11*     (2006.01)
    *A61B 5/00*     (2006.01)
    *G16H 40/63*     (2018.01)

(52) U.S. Cl.
CPC ....... *A61H 31/007* (2013.01); *A61N 1/37247* (2013.01); *A61N 1/37258* (2013.01); *A61N 1/3993* (2013.01); *G16H 40/63* (2018.01); *A61H 2201/0184* (2013.01); *A61H 2201/501* (2013.01); *A61H 2201/5007* (2013.01); *A61H 2201/5035* (2013.01); *A61H 2201/5038* (2013.01); *A61H 2201/5043* (2013.01); *A61H 2201/5048* (2013.01); *A61H 2201/5061* (2013.01); *A61H 2201/5071* (2013.01); *A61H 2201/5076* (2013.01); *A61H 2201/5079* (2013.01); *A61H 2201/5097* (2013.01); *A61H 2230/045* (2013.01)

(58) Field of Classification Search
CPC .... A61H 2201/5048; A61H 2201/5035; A61H 2201/0184; A61H 2201/5038; A61H 2201/5007; A61H 2201/5061; A61H 2201/5071; A61H 2201/5097; A61H 2230/045; A61H 2201/501; A61B 5/742; A61B 5/6843; A61N 1/3993; A61N 1/37247; A61N 1/37258
See application file for complete search history.

(56) References Cited

U.S. PATENT DOCUMENTS

| | | |
|---|---|---|
| 2007/0010764 A1 | 1/2007 | Palazzolo et al. |
| 2007/0060785 A1* | 3/2007 | Freeman ............... A61H 31/00 600/16 |
| 2008/0146974 A1* | 6/2008 | Lund .................... A61H 31/00 601/41 |
| 2008/0171311 A1 | 7/2008 | Centen et al. |
| 2010/0160839 A1 | 6/2010 | Freeman et al. |
| 2010/0211127 A1 | 8/2010 | Eerden |
| 2011/0040217 A1 | 2/2011 | Centen |
| 2011/0301511 A1 | 12/2011 | Freeman |
| 2012/0010543 A1* | 1/2012 | Johnson ............... A61N 1/3925 601/41 |

* cited by examiner

10

30

40

60

50

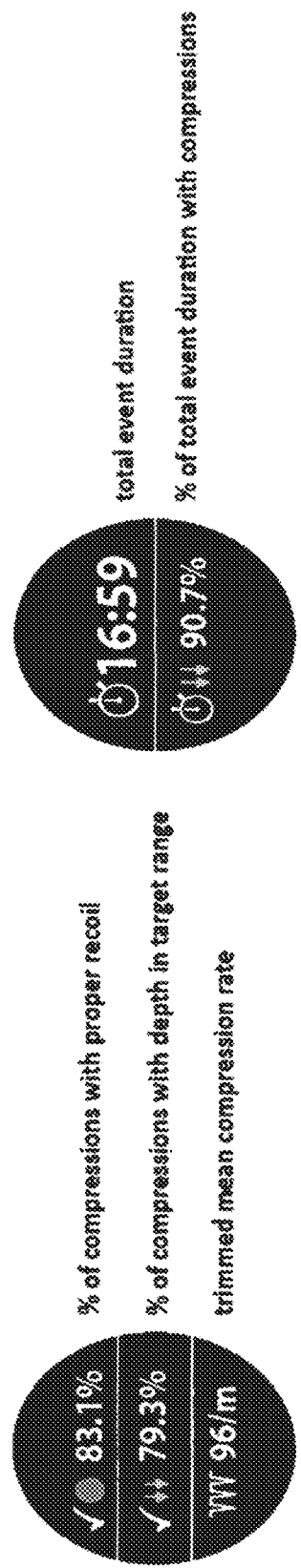

PROGRAMMABLE CARDIOPULMONARY RESUSCITATION (CPR) DETECTION DEVICE

CROSS-REFERENCE TO RELATED APPLICATIONS

This disclosure claims priority from U.S. patent application Ser. No. 13/306,933, now U.S. Pat. No. 9,149,411, filed Nov. 29, 2011, which claims benefit of U.S. Provisional Application Ser. No. 61/417,801, filed Nov. 29, 2010; each disclosure of which is hereby incorporated by reference in their entirety.

TECHNICAL FIELD

The present invention relates generally to cardiopulmonary resuscitation (CPR) feedback systems.

BACKGROUND

By forcing blood through the circulatory system and thereby maintaining oxygen distribution throughout a patient's body, cardiopulmonary resuscitation (CPR) can drastically improve the chance of survival for the patient experiencing cardiac failure.

According to the 2010 American Heart Association Guidelines for Cardiopulmonary Resuscitation and Emergency Cardiovascular Care, in most emergencies, the quality of CPR provided by the rescuer can make the difference between life and death. An effective compression rate is recommended as that of 100 chest compressions per minute at a compression depth of about 4-5 cm. Unfortunately, even trained professionals often do not perform CPR correctly. An automated audio-visual CPR feedback device can greatly assist a rescuer in correcting his or her CPR administering technique and thereby improve a patient's chance of survival.

Attempts are being made to develop and improve CPR automated-feedback devices. The chest compression rate is highly correlated to the spontaneous return of circulation after cardiac arrest. CPR feedback devices to-date are stand-alone devices, unable of real-time communication and corroboration with other devices, including medical devices. Often, CPR is administered when unnecessary or is not administered when necessary. Studies have found that compressions are often not delivered when cardiovascular circulation was absent. Corroboration with other devices would be highly desirable in selecting the most appropriate course of therapy. Further, existing CPR feedback devices lack programmable user-interfacing and setting options. Such device/user interfacing would be most desirable in providing patient and user custom-tailored and flexible CPR feedback most fit to both the patient and the rescuer.

Time after time studies find that often, even when administered by trained professionals, cardiopulmonary resuscitation (CPR) compression rates and depth are inadequate. Too week, shallow or too forceful compressions may contribute to suboptimal patient outcome. Several parameters are crucial for optimal and properly-administered CPR. Crucial parameters include proper hand positioning on the patient's chest, depth of compression of 4-5 cm, and compression rate of 100 compressions per minute. The crucial parameters are often affected by patient parameters, and relative to the patient, rescuer parameters, such as patient thoracic volume; weight; age; gender; and rescuer's, relative to the patient's, parameters, such as weight, height; physical form, etc.

Proposed here is an automated CPR feedback device with user programmable settings for assisting with real-time feedback and subsequently correcting rescuers patient customized CPR technique.

Accordingly, a CPR feedback device that is capable of being pre-programmed by a user and further able to communicate with additional devices would be highly desirable. Furthermore, other desirable features and characteristics of the present invention will become apparent from the subsequent detailed description and the appended claims, taken in conjunction with the accompanying drawings and the foregoing technical field and background.

BRIEF SUMMARY

A programmable device for cardiopulmonary resuscitation ("CPR device") integrates a voice module and an automated rescue feedback. In one embodiment the CPR device is programmed to automatically provide real-time synchronization with an Automated External Monitor/Defibrillator (AED), allowing the AED to take control over the CPR device. The AED becomes a master controlling device dictating the rate and assessing performance of the CPR device. Feedback on chest compression rate, depth and quality are transmitted to the master controlling device, which then assesses and guides a user in providing an optimal quality CPR compression rate and performance, and further assess and select a best-fit treatment protocol.

In one embodiment, a user pre-programs voice prompts, compression rate, tones, rhythm, volume, and other biophysical parameters needed for resuscitation or communications. Configuration of the CPR device can also be managed remotely, either by a hand-held device, or a computer, such as a laptop or desktop.

The CPR feedback device includes an application interface, allowing real-time display of information on a remote display, which may include an AED, a hand-held device such as a mobile phone, a personal computer, a laptop. The data can be displayed in real time as well as post-event. The display of CPR activity, in one embodiment, comprises depth compression waveforms, force compression waveforms, biophysical parameters, inactive time, elapsed time, compressions delivered, ventilations delivered, proper hand repositioning warnings.

In a further embodiment, the CPR device settings can be changed by a user. The settings comprise target or range of compression depth; fixed compression depth range; relative to chest size and thickness compression depth range, compression rate, prompting language, prompting volume level, time allowed for inactivity; audio alarms; visual alarms; event timing; custom configuration to an individual patient; ventilation prompts; on and off prompts; number of ventilations, number of compressions before ventilations. Other CPR activity and settings may be pre-set.

In a further embodiment, the CPR device communicates with a plurality of external and internal devices. For example, the CPR device is able through either wired or wireless settings to communicate with other devices. The CPR device is capable of receiving and sending data. The CPR device is further able to receive data regarding settings and is programmed and reprogrammed by another device within a network. The data can also be stored and transferred from the CPR device for a post-event review and analysis.

In a further embodiment, the CPR device and an AED are synchronized and corroborate to carry out the most optimal CPR and shock delivery and therapy engaging different therapy protocols depending on baseline assessment of the individual patient. Different therapy protocols can be automatically recommended and engaged based upon patient parameters detected by both the CPR device and an AED. Thus, based on corroboration between the CPR device with an AED, accelerates decision-making and therapy within crucial to the patient time window. For example, based on the data acquired by the CPR device/AED combination, a stimulus signal is applied to a patient. The stimulus signal elicits mechanical and electrical cardiac response from the heart. The stimulus signal maintains mechanical capture until defibrillation therapy is administered. The application of the stimulus signal is desirable to enhance the patient's responsiveness to the defibrillation therapy, and is used instead of continuing CPR.

Still other embodiments of the present invention will become readily apparent to those skilled in the art from the following detailed description, wherein is described embodiments of the invention by way of illustrating the best mode contemplated for carrying out the invention. As will realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

FIG. 7 is an illustration of post-event data obtained using one of the resuscitation protocols selected via optimization process, in accordance with one embodiment.

DETAILED DESCRIPTION

Figure 1:
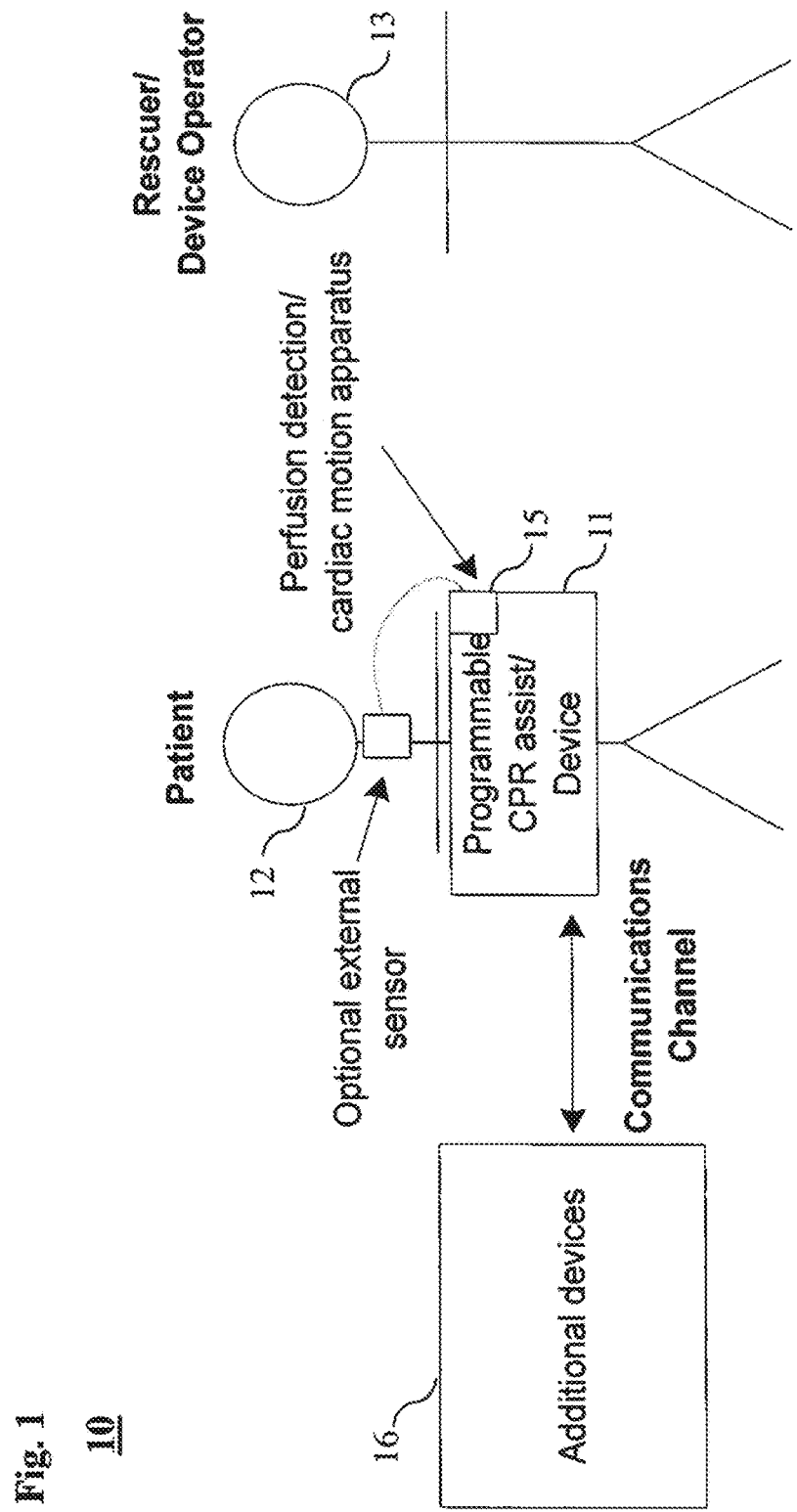
FIG. 1 is an illustration of a programmable CPR device applied to an emergency event environment, in accordance with one embodiment.

The following detailed description is merely exemplary in nature and is not intended to limit the invention or the application and uses of the invention. For example, a practical embodiment of the invention may be deployed in connection with CPR feedback device, an automatic or automated external defibrillator, a semi-automatic or semi-automated external defibrillator, a manual external defibrillator, patient monitoring systems, and possibly implantable defibrillator devices. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of practical CPR, defibrillator systems, emergency and hospital wired and wireless networks, and that the system described herein is merely one exemplary application for the invention.

For the sake of brevity, conventional techniques related to CPR devices and systems, detection of non-perfusing cardiac rhythms, estimation of the probability of defibrillation pulse success based on VF waveform characteristics, defibrillator device operation, the detection of electrical capture of the heart, the detection of mechanical capture of the heart, resuscitation techniques and protocols, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

As mentioned above, a device configured in accordance with the invention detects, in response to a diagnostic signal applied to the patient, physiologic responses from the patient. As used herein, a "physiologic response" means a measurable or detectable reaction, condition, effect, or characteristic of the patient or any biological system of the patient, including, for example, a neurological response, a muscular response, a cardiac response, or the like. Resuscitation protocols include one of or a combination of CPR, drugs, defibrillation therapy, or the like.

FIG. 1 depicts a programmable CPR assist/device in a network system 10 that is configured to optimize and deliver CPR/defibrillation therapy to a patient 12, such as a victim of ventricular fibrillation ("VF"). The environment system 10 includes, but is not limited to, a the CPR feedback device ("CPR device") 11, external sensors and perfusion sensors 15, and any additional devices 16 such as by way of example an external defibrillator device having a wired and/or wireless communication channel between one or more devices and external network communicating with emergency and hospital unit (not shown). The environment system 10 further includes a user who is the rescuer, or device operator. As used herein, a "user" of a CPR feedback device or defibrillator or monitoring system includes, without limitation: an operator, a caregiver; a rescuer; medical personnel; a clinician; or any person having manipulative access to the CPR device, defibrillator or monitoring system. Unless otherwise indicated, these terms may be interchangeably used in the following description.

A therapy protocol may begin be recommended for initiating CPR in lieu of immediate defibrillation. In situations where electrical cardiac response is not obtained, it might be better to administer CPR and possibly other modes of therapy rather than spend valuable time performing defibrillation. In practice, CPR is performed by the caregiver. In addition to CPR, it may be recommend or administer other modes of therapy prior to defibrillation. For example, one or more of the following may be performed at this time: CPR; ventilation; drug therapy; pacing; PESP; or other electrical therapy. In a practical embodiment, resuscitation process may be re-entered at query task after an appropriate amount of CPR has been administered to the patient. Consequently, the diagnostic techniques described above can be utilized before and/or after defibrillation therapy.

Figure 2:
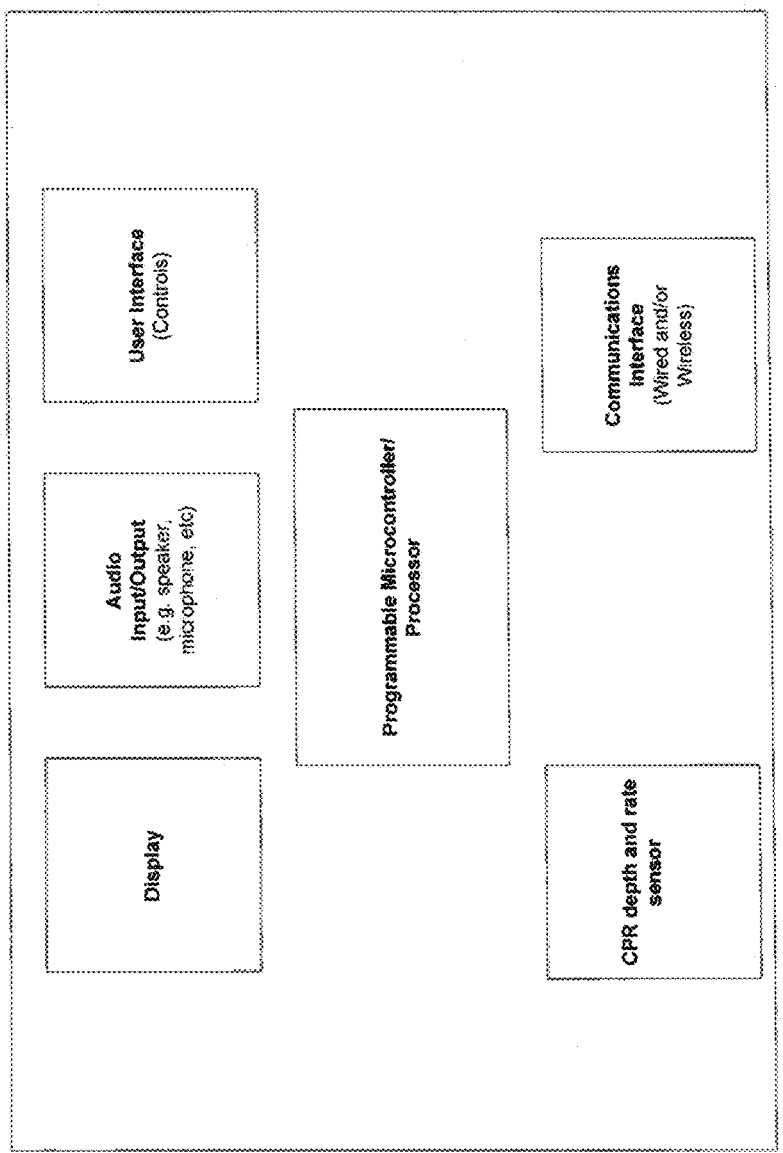
FIG. 2 is a block representation of a programmable CPR device, in accordance with an example embodiment of the invention.

FIG. 2 is a block diagram for the programmable CPR device 20, comprising a display, an audio input/output, such as a speaker and a microphone, user interface including controls, programmable microcontroller/processor for entering setting variables and processing inputs and output, a CPR depth and rate sensor, and a communications interface, which could be wired or wireless. The CPR device settings can be changed by a user or a remote device. The settings comprise target or range of compression depth; fixed compression depth range; relative to chest size and thickness compression depth range, compression rate, prompting language, prompting volume level, time allowed for inactivity; audio alarms; visual alarms; event timing; custom configuration to an individual patient; ventilation prompts; on and off prompts; number of ventilations, number of compressions before ventilations. Other settings apparent to one skilled in the art are possible.

Several parameters are crucial targets for optimal and properly-administered CPR. Target parameters include proper hand positioning on the patient's chest, depth of compression of 4-5 cm, and compression rate of 100 compressions per minute. The crucial parameter settings are often affected by patient parameters, and relative to the patient, rescuer parameters, such as patient thoracic volume; weight; age; gender; and rescuer's, relative to the patient's, parameters, such as weight, height; physical form, etc. Proposed here is an automated CPR feedback device with user programmable settings for assisting with real-time feedback and subsequently correcting rescuers patient customized CPR technique. Other settings apparent to one skilled in the art are possible.

Figure 3:
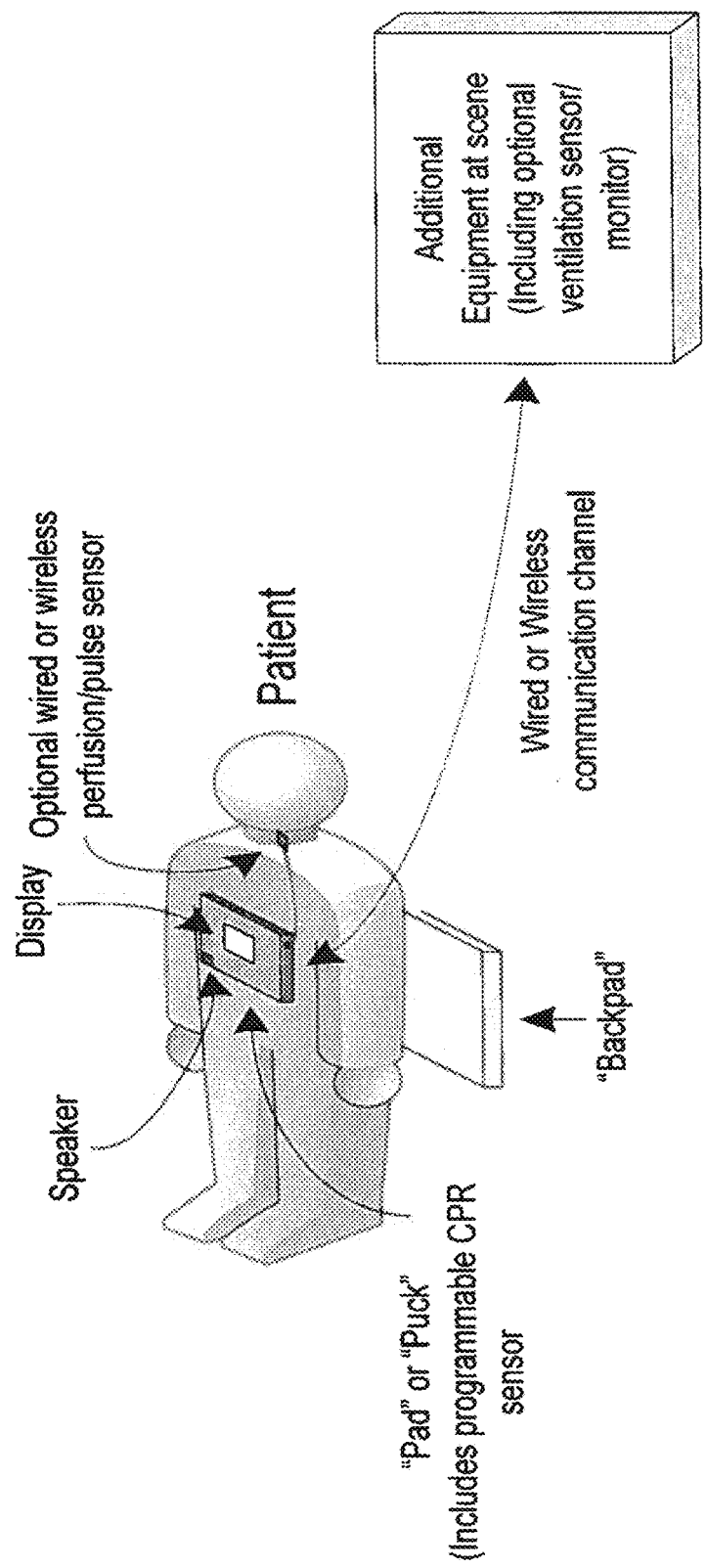
FIG. 3 is a block diagram of one embodiment of a programmable CPR device, according to an example embodiment of the invention.

FIG. 3 is an illustration of one embodiment of the programmable CPR device 11 positioned on a patient's chest. The CPR device includes a visual display, a speaker and a programmable CPR sensor, which may also be called a "pad" or "puck." A backpad is used when needed to ensure proper reflective support against compressions. In one embodiment, a resuscitation protocol performed when the patient does not respond to the diagnostic signal, i.e., neither mechanical cardiac response nor electrical cardiac response is detected.

Figure 4:
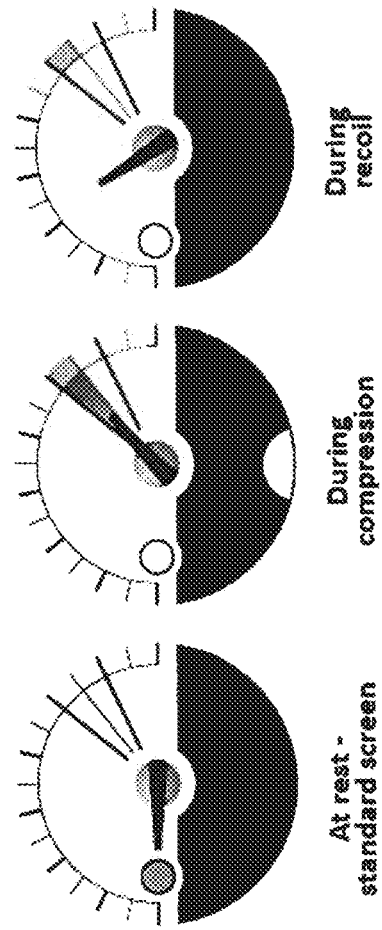
FIG. 4-6 are illustrative examples of one embodiment of CPR device representations of feedback to a user.
Figure 6:
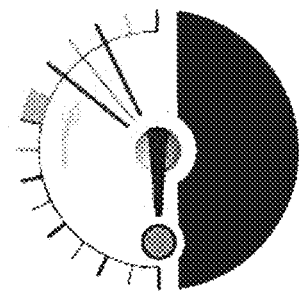
Figure 5:
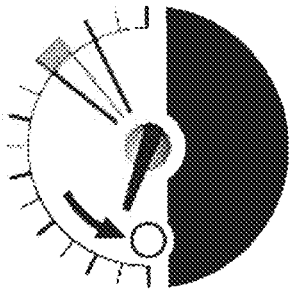

The CPR device preferably includes a user interface. FIGS. 4-6 are illustrations of one type of visual display and feedback to the user. In this embodiment, the visual display is configured to represent outputs measured during resuscitation event. The information is available to the user who then can visually verify or improve his or her compressions rhythm and depth as exerted on a patient in real-time. For example, display can feature a dial, or a speedometer indicating relative compression depths with ranges indicative of rest state, optimal compression, and recoil. A counter per minute can sound out each compression and a series of sequential rhythm or sounds for each compression cycle. The hand or arrow in the dial or speedometer responds to each compression cycle and shows the user whether optimal or sub-optimal compression has been achieved. The display can further keep track of number of compressions and issue commands and responses which can either instruct to correct or maintain the rhythm and depth. In a further embodiment, voice prompts and feedback are included. In one example, a rhythmic sound of compressions is accompanied with feedback advising of the percentage of recoil, or depth target reached. Other visual and audio representations are possible.

FIG. 7 illustrates one embodiment of post-event feedback comprising percentage of compressions with proper recoil; percent of compressions with depth in target range; trimmed mean compression rate; total event duration; and percentage of total duration with compressions.

Alternatively, or additionally, post-event data may be transferred to a remote computing device using portable storage media. For example, the post-event data can be transferred or copied from memory onto a portable storage device for transport to the remote computing device.

Although the present invention has been particularly shown and described with reference to embodiments, those skilled in the art will understand that the foregoing and other changes in form and detail may be made therein without departing from the spirit and scope of this disclosure. Further, presently unforeseen or unanticipated alternatives, modifications, variations, or obvious improvements therein may be subsequently made by those skilled in the art, which are also intended to be encompassed by the following claims.

The invention claimed is:

1. A cardiopulmonary resuscitation (CPR) system, comprising:
   an external device configured to communicate through a communication channel with one or more other devices and to transmit one or both of programming instructions or re-programming instructions from the one or more other devices;
   a programmable CPR device configured to communicate with the external device through the communication channel, the programmable CPR device including:
   (a) a cardiopulmonary resuscitation (CPR) sensor configured to output CPR sensor data indicative of depth and rate of compressions exerted on a patient,
   (b) a processor configured:
      to receive customized user programmed settings;
      to analyze the CPR sensor data;
      to apply, in real-time, the customized user programmed settings to one or more parameters of the CPR sensor data, the one or more parameters including one or both of the depth and rate of compressions exerted on the patient; and
      to generate real-time, customized CPR feedback data based on the real-time application of the customized user programmed settings to the one or more parameters of the CPR sensor data; and
   (c) a communication module electrically coupled to the communication channel and configured to receive the programming instructions or the re-programming instructions through the communication channel, and
   a therapy resuscitation delivery module configured to select and automate a therapy route based on the real-time, customized feedback CPR data;
   wherein the external device includes an external defibrillator configured to transmit the re-programming instructions to reprogram the programmable CPR device, the transmitted re-programming instructions including instructions to reprogram the customized user programmed settings of the programmable CPR device.

2. The Cardiopulmonary Resuscitation (CPR) system of claim 1 in which the external defibrillator and the programmable CPR device are configured to be synchronized to administer CPR and shock delivery based on a baseline assessment of the patient.

3. The Cardiopulmonary Resuscitation (CPR) system of claim 1 in which the external device is wirelessly connected to the programmable CPR device through the communication channel.

4. The Cardiopulmonary Resuscitation (CPR) system of claim 1 in which the external device and the programmable CPR device are connected to the communication channel through a wired connection.

5. The Cardiopulmonary Resuscitation (CPR) system of claim 1 further comprising a plurality of external devices, in which at least one of the plurality of external devices is configured to communicate through the communication channel to transmit the programming instructions or the reprogramming instructions to the programmable CPR device.

6. The Cardiopulmonary Resuscitation (CPR) system of claim 5 in which at least two of the plurality of external devices are configured to communicate through the communication channel to transmit the programming instructions or the reprogramming instructions to the programmable CPR device.

7. The Cardiopulmonary Resuscitation (CPR) system of claim 1 in which the programmable CPR device further includes a display component configured to display real-time feedback to a user, the real-time feedback indicative of qualities of compression depth and rate and, the display further configured to display post-event data.

* * * * *